US012616605B2

(12) United States Patent
Clare et al.

(10) Patent No.: US 12,616,605 B2
(45) Date of Patent: May 5, 2026

(54) MANDIBULAR REPOSITIONING DEVICE

(71) Applicant: James R. Glidewell Dental Ceramics, Inc., Newport Beach, CA (US)

(72) Inventors: Randy C. Clare, San Juan Capistrano, CA (US); Kenad Destanovic, Mission Viejo, CA (US); Vaheh Golestanian Nemagrdi, Orange, CA (US)

(73) Assignee: James R. Glidewell Dental Ceramics, Inc., Newport Beach, CA (US)

( * ) Notice: Subject to any disclaimer, the term of this patent is extended or adjusted under 35 U.S.C. 154(b) by 102 days.

(21) Appl. No.: 17/131,197

(22) Filed: Dec. 22, 2020

(65) Prior Publication Data

US 2022/0192863 A1 Jun. 23, 2022

(51) Int. Cl.
A61F 5/56 (2006.01)
(52) U.S. Cl.
CPC .................................... A61F 5/566 (2013.01)
(58) Field of Classification Search
CPC ...... A61F 5/566; A61F 5/56; A61F 2005/563;
A61F 5/58; A61C 7/08; A61C 7/36
USPC ........................................................ 128/848
See application file for complete search history.

(56) References Cited

U.S. PATENT DOCUMENTS 6,109,265 A  8/2000  Frantz et al.
6,418,933 B1 *  7/2002  Strong ..................... A61F 5/566
128/848

7,178,529 B2  2/2007  Kownacki
7,597,103 B2  10/2009  Thornton et al.
8,783,261 B2  7/2014  Thornton
2003/0207224 A1 *  11/2003  Lotte ......................... A61C 7/08
433/6
2015/0216716 A1 *  8/2015  Anitua Aldecoa ....... A61C 7/08
128/848
2017/0007442 A1 *  1/2017  Dietz ...................... A61F 5/566
2018/0207022 A1 *  7/2018  Alvarez .................. A61F 5/566
2019/0110866 A1 *  4/2019  Nagai ...................... A61C 7/08
2019/0336321 A1 *  11/2019  Garvey .................. A61F 5/566
2020/0323677 A1 *  10/2020  Droter ..................... A61C 7/36
2021/0353387 A1 *  11/2021  Velamakanni ....... A61C 19/063

* cited by examiner

*Primary Examiner* — Victoria Hicks Fisher
(74) *Attorney, Agent, or Firm* — Klarquist Sparkman, LLP

(57) ABSTRACT

A dental appliance to reduce or eliminate snoring is disclosed. The dental appliance includes an upper tray, a lower tray, one or more tray-removal features, and a connecting arm. The upper tray includes a first coupling post located on a buccal surface of the upper tray. The lower tray includes a second coupling post located on a buccal surface of the lower tray. Each of the coupling posts includes a flange configured to pivotably and slidably secure the connecting arm and to release the connecting arm when the upper tray is rotated to a predetermined angle with respect to a closed position of the upper and lower trays. The one or more tray-removal features are disposed on the buccal or lingual surface of each of the upper and lower trays.

14 Claims, 9 Drawing Sheets

450

800

450

MANDIBULAR REPOSITIONING DEVICE

TECHNICAL FIELD

The disclosure generally relates to the field of dental appliances, specifically and not by way of limitation, some embodiments are related to a dental appliance that reduces snoring and/or helps treat sleep apnea.

BACKGROUND

Snoring affects a very large group of people, the prevalence of habitual snoring is 8.9% in females and 29.5% in males, and presents a significant public health issue. People with chronic snoring can have serious health problems such as sleep apnea, which is a condition characterized by the cessation of breathing for 10 seconds or longer. Patients with untreated sleep apnea are at increased risk of hypertension, stroke, heart failure, diabetes, car accidents and depression.

Snoring, also referred to as stertor by medical professionals, is caused by partially blocked airways, which occur when muscles along the airways (e.g., jaw, throat) relax during sleep and partially collapse into the airway and start to vibrate as the person breathes. Certain physiological conditions are prone to having partially obstructing the upper airways such as an abnormally large tonsil (uvula) or tongue, a small upper airway, a recessed chin, large overbite or a narrow maxillary arch with a high palatal vault.

Two of the most common treatments for snoring or sleep apnea are continuous positive airway pressure (CPAP) devices and dental devices that adjust the position of the lower jaw forward during sleep. These dental devices are better known as mandibular repositioning or mandibular advancement devices (MA devices), which are designed to position the lower jaw forward to activate the muscles and ligaments of the upper airway providing the tone necessary to avoid the collapse of flaccid tissues during sleep. CPAP devices are considered the gold standard of therapy for obstructive sleep apnea, however 50% of patients abandon therapy within 3 months of receiving the device due to discomfort and side effects associated with the therapy.

MA devices are available to the public for the treatment of snoring and sleep apnea. However, currently available (conventional) mandibular advancement devices have deficiencies such as connectors that are inaccurate or stretch over time between upper and lower trays of the mandibular advancement device, connectors that can be damaged when changed or adjusted or upper and lower trays that have soft tissue contact which can lead to hotspots and inflammation. These design flaws can discourage users from continuously using the MA device or worse can cause users to discontinue treatment altogether. Accordingly, what is needed is a MA device that is more comfortable, secure, yet easy for the clinician to install, adjust chairside and titrate as treatment progresses, This device should fit into modern design and manufacturing workflows such that it is easy to manufacture (which increases the device's quality and reduces manufacturing cost delivering more value to the clinician).

SUMMARY

Disclosed are example embodiments of a manufacture to reduce snoring. In one example embodiment, the manufacture includes an upper tray, a lower tray, and a connecting arm. The upper tray is configured to engage a plurality of maxillary teeth and includes a first coupling post located on a buccal surface of the upper tray. The lower tray is configured to engage a plurality of mandibular teeth and includes a second coupling post located on a buccal surface of the lower tray. The first coupling post is closer to a midline of the upper tray than the second coupling post.

The connecting arm is configured to slidably and pivotably couple the upper and lower trays to each other. The connecting arm can include a first slot and a second slot. One or more of the first and second coupling posts can include a flange that is configured to pivotably and slidably secure the connecting arm and to release the connecting arm when it is rotated to a predetermined angle with respect to a closed position of the upper and lower trays. The predetermined angle can be any angle greater than 45 degrees, which is greater than the maximum angle a human mouth can be opened.

The first and second slots of the connecting arm can be parallel to each other. In some embodiments, the first and second slots are not arranged parallel to each other. Both of first and second coupling posts can also include a flange, which can have a width smaller than a width of each slot and a length longer than the width of each slot. This enables the flange to fit into the slot when rotated at a certain angle. The coupling post can be a T-shape post.

The first and second slots can be independent from each other. Alternatively, the first and second slots can be one continuous slot. In some embodiments, the continuous slot can be a Z-shape slot.

Each of the upper and lower trays can also include one or more tray-removal features. The one or more tray-removal features can be disposed on the buccal surface of each of the upper and lower trays. The one or more tray-removal features can also be disposed on a lingual surface of each of the upper and lower trays.

The one or more tray-removal features can be grooves, which enable a user to grip the upper or lower tray. The one or more tray-removal features can also be raised portions (e.g., ridges, edges) to enable the user to grip the upper or lower tray.

The upper tray can include a flat-bottom surface. Similarly, the lower tray can also include a flat-upper surface. The flat-bottom and flat-upper surfaces are parallel to each other when the upper and lower trays are in a closed position.

In another example, a dental appliance for adjusting the position of a lower jaw with respect to the upper jaw is disclosed. The dental appliance includes: an upper tray configured to engage a plurality of maxillary teeth; a lower tray configured to engage a plurality of mandibular teeth; a one or more tray-removal features disposed on a buccal or lingual surface of each of the upper and lower trays; and a connecting arm configured to couple the upper and lower trays. The upper tray can include a first coupling post located on a buccal surface of the upper tray and a flat-bottom surface. The lower tray can include a second coupling post located on a buccal surface of the lower tray and a flat-upper surface. The connecting arms can include a first slot and a second slot parallel to each other. The first coupling is closer to a midline of the upper tray than the second coupling. Additionally, the flat-upper and flat-bottom surfaces are parallel to each other when the upper and lower tray are in a closed position.

In yet another example, a dental appliance for adjusting a position of a lower jaw is disclosed. The dental appliance includes: an upper tray configured to engage a plurality of maxillary teeth, the upper tray comprises a first coupling post located on a buccal surface of the upper tray; a lower tray configured to engage a plurality of mandibular teeth, the lower tray comprises a second coupling post located on a buccal surface of the lower tray; one or more tray-removal features disposed on a buccal or lingual surface of each of the upper and lower trays; and a connecting arm configured to couple the upper and lower trays, the connecting arms comprises a first slot and a second slot parallel to each other. In this example embodiment, the coupling posts includes a flange configured to pivotably and slidably secure the connecting arm and to release the connecting arm when the upper tray is rotated to a predetermined angle with respect to a closed position of the upper and lower trays.

The features and advantages described in the specification are not all inclusive and, in particular, many additional features and advantages will be apparent to one of ordinary skill in the art in view of the drawings, specification, and claims. Moreover, it should be noted that the language used in the specification has been principally selected for readability and instructional purposes and may not have been selected to delineate or circumscribe the disclosed subject matter.

BRIEF DESCRIPTION OF THE DRAWINGS

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

DETAILED DESCRIPTION

In the following description, for purposes of explanation, numerous specific details are set forth to provide a thorough understanding of the invention. However, it will be apparent to one skilled in the art that the invention can be practiced without these specific details. In other instances, structures and devices are shown in a block diagram form in order to avoid obscuring the invention.

Figure 1:
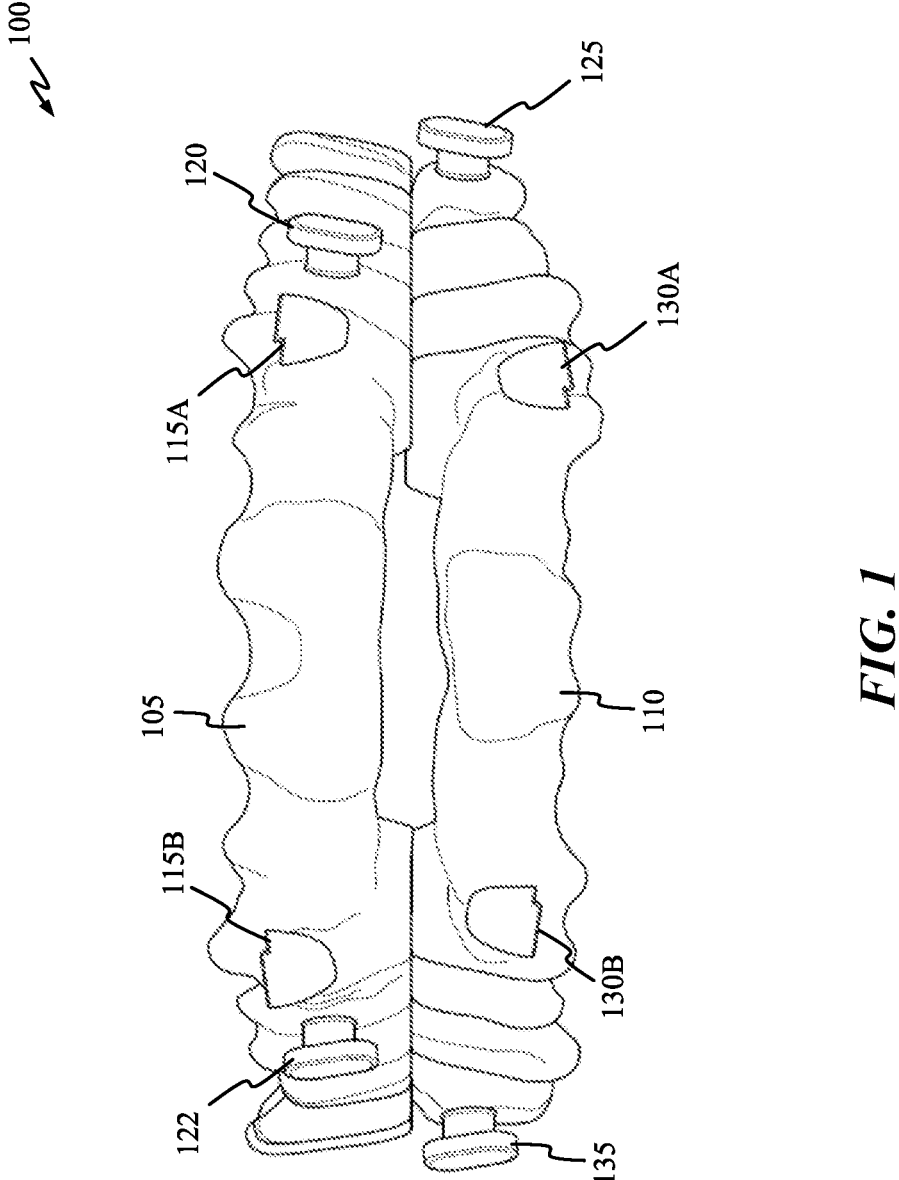
FIG. 1 is a front view of a mandibular advancement device in accordance with some embodiments of the present disclosure.

FIG. 1 is front view of the mandibular advancement (MA) device 100 in accordance with some embodiments of the present disclosure. Mandibular advancement device 100 includes upper tray 105 and lower tray 110. Upper tray 105 can be specifically made for a patient by molding the interior surfaces (not shown) to match the dentition surfaces of some (or all) of the patient's maxillary teeth. This can be done using a mold formed from a dentition impression or from a scanned 3D model of the patient's dentition. Similarly, lower tray 110 can also be specifically molded to fit dentition surfaces of some of the patient's mandibular teeth. In other words, lower tray 110 is fabricated to include inner surfaces (see item 205 of FIG. 2) to match the patient's dentition using dental impression or a scanned 3D model of the patient's dentition.

Upper tray 105 includes coupling posts 120, 122 and one or more tray-removal features 115A, 115B. Similarly, lower tray 110 includes coupling posts 125, 135 and one or more tray-removal features 130A, 130B. Each of trays 105 and 110 can have a single or a plurality of tray-removal features 115A, 115B. For example, upper tray 105 can include only 1 tray-removal feature 115A that can be disposed anywhere on the buccal surface upper tray 105. In some embodiments, the single tray-removal feature 115 can be disposed near the midline of upper tray 105. Similarly, lower tray 110 can include a single tray-removal feature 130, which can also be disposed on or near the midline of lower tray 110.

Figure 2:
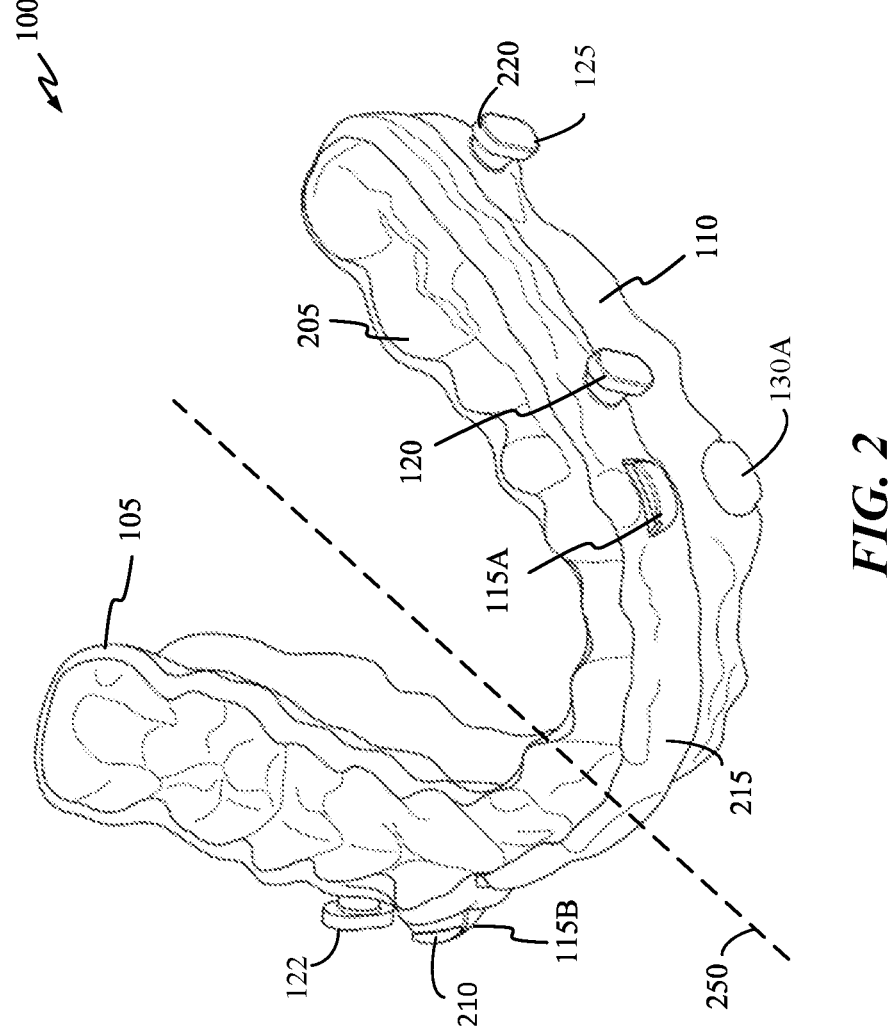
FIG. 2 is a perspective view of the mandibular advancement device shown in FIG. 1 in accordance with some embodiments of the present disclosure.

FIG. 2 is a top perspective view of device 100, which looks down into upper tray 105. As shown, upper tray 105 include surface area 205 with detailed dentition surfaces and/or features to match and mate with the surfaces of the patient's maxillary teeth. Lower tray 110 also includes similar inner surfaces (hidden from view) to match and mate with the surfaces of the patient's mandibular teeth.

Figure 3:
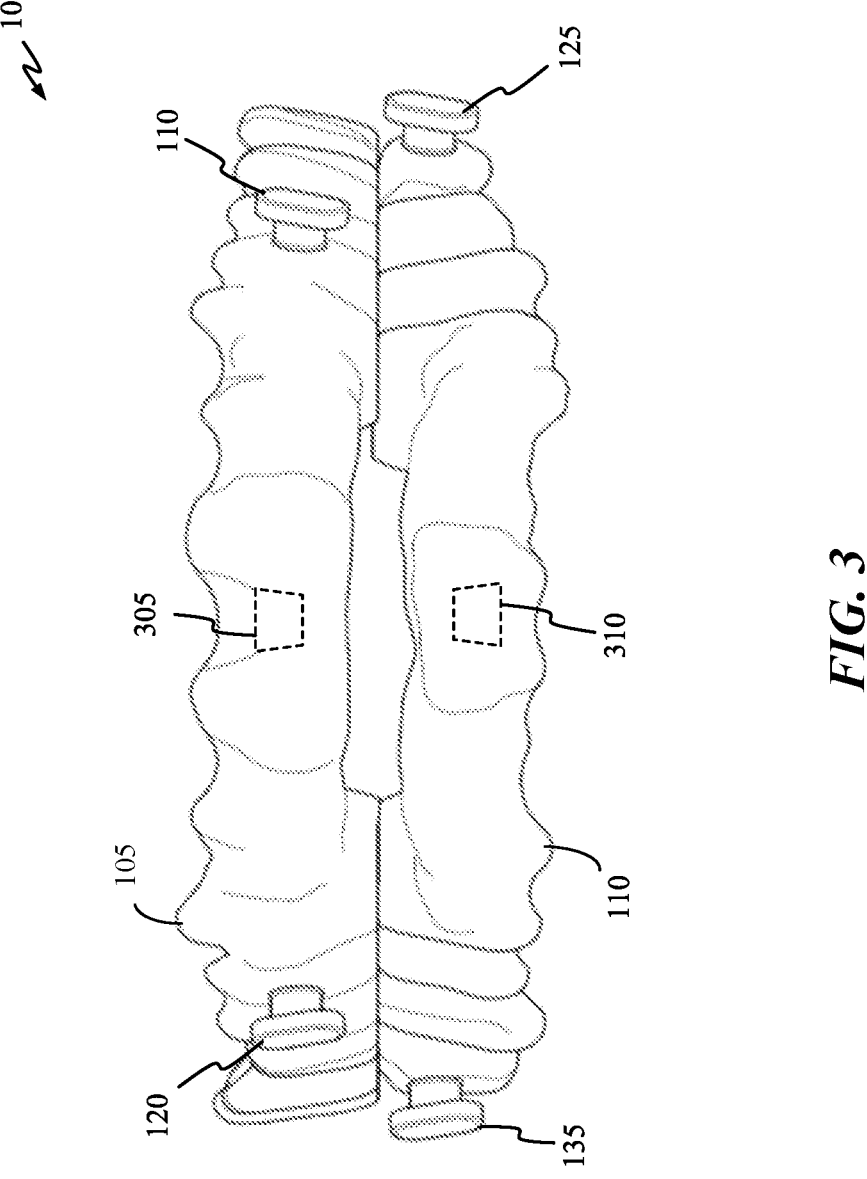
FIG. 3 is a front view of a mandibular advancement device in accordance with some embodiments of the present disclosure.

FIG. 3 is a front view of MA device 100 without tray-removal features on the buccal surface in accordance with some embodiments of the present disclosure. As shown, device 100 includes one or more tray-removal features 305, 310 on the lingual surface of each of the upper and lower trays 105, 110. As shown, upper tray 105 includes tray-removal feature 305 on the lingual surface on or near the midline. Similarly, tray-removal feature 310 is on the lingual surface of lower tray 110. In some embodiments, a hand-held wand (not shown) designed to engage with tray-removal features 305, 310 can be provided. The hand-held wand can include a small head that can easily be inserted into the patient's mouth and behind upper or lower tray 105, 110. The head of the hand-held wand can hook onto an edge of tray-removal feature 305 or 310. In this way, when the user pull on the hand-held wand, the upper or lower tray 105, 110 can be dislodged from the patient's teeth.

In some embodiments, the tray-removal feature (e.g., 115, 130, 305, 310) can be a groove (e.g., channel, slot) on the surface of the upper or lower tray 105, 110. The groove can be sized just sufficiently large for a fingernail to catch into the groove, which enables the patient's to pull away the upper or lower tray 105, 110. The tray-remove feature can also be a raised ridge (e.g., edge, bar, shape). In some embodiments, the raised ridge can have a slope that slowly blends onto the surface of the upper or lower tray 105, 110. In this way, the patient's cannot easily feel the tray-removal feature.

Referring to FIG. 2, tray-removal feature (e.g., raised ridge) 115 can have a trapezoidal shape with the top portion 210 of the trapezoid extending out from buccal surface 215 of upper tray 105. This creates an edge or surface on which the patient can grab. This enables the patient's to easily remove the upper or lower tray 105, 110. Accordingly, in some embodiments, the tray-removal feature may comprise a raised ridge having a top portion extending outward in a buccal direction from the buccal surface or a lingual direction from the lingual surface of the upper or lower tray, thereby defining an edge to be grasped by the patient.

As shown, coupling posts 120 and 122 of upper tray 105 are closer to midline 250 than coupling post 125 and 135 (hidden from view, but see FIG. 1). Each of the coupling posts can have a flange 220 at the distal end of the post, and the proximal end of the post is attached to buccal surface 215 of the upper or lower tray 105, 110. In some embodiments, the coupling post can have a T-shape. In other words, flange 220 extends outward and perpendicular to the axis of the post.

Figure 4:
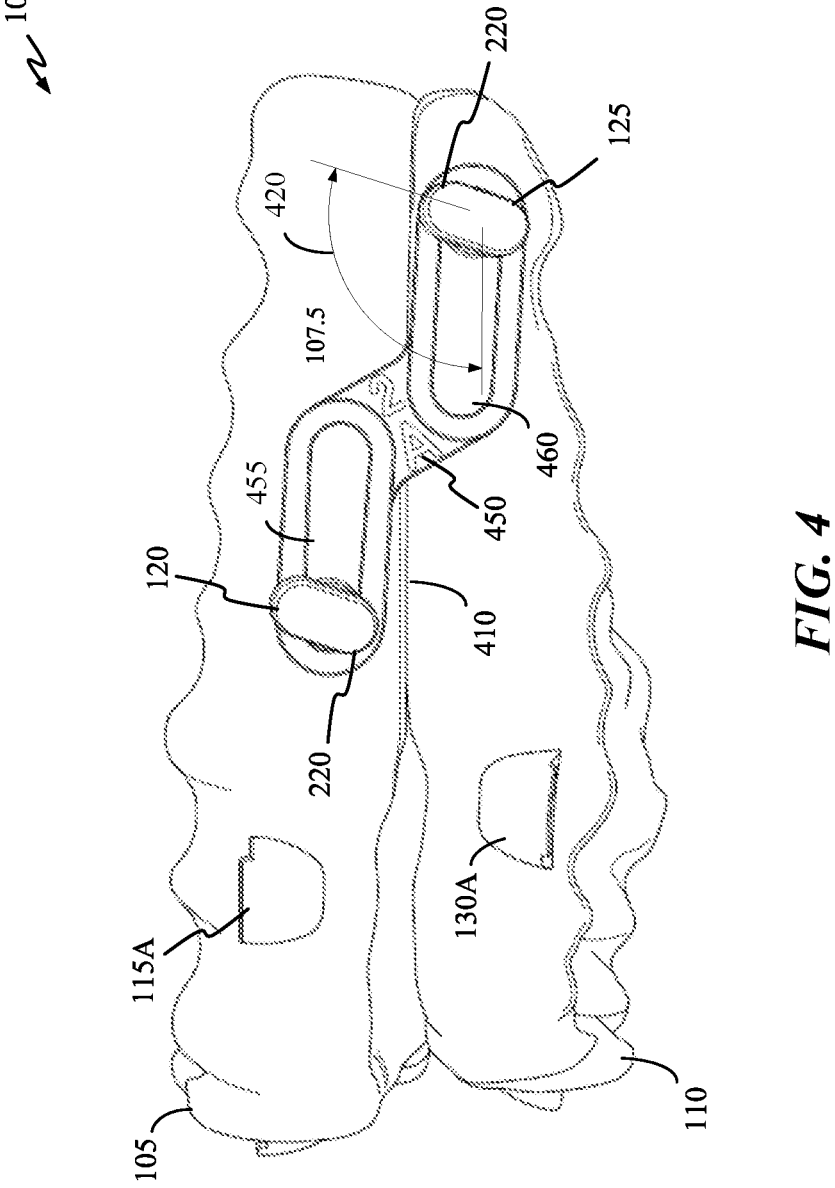
FIG. 4 is a side view of a mandibular advancement device in accordance with some embodiments of the present disclosure.

FIG. 4 is a side view of MA device 100. In some embodiments, flange 220 of each coupling post (e.g., post 125) can be arranged at a predetermined angle 420 with respect to the horizontal plane 410. Angle 420 can have a range between 45-170 degrees. For example, angle 420 can be between 45-120 degrees. In some embodiments, angle 420 is 60 degrees or 107.5 degrees. Angle 420 can be influenced by the maximum angle on which the patient can fully open his/her mouth. For example, the widest mouth opening a human open is typically less than 45 degrees. In some embodiments, angle 420 is set at an angle greater than the maximum mouth-opening angle, which can be measured with respect to plane 415. As shown in FIG. 4, flange 220 be angled at 107.5 degrees with respect to plane 415. Flange 220 on coupling post 120 can be similarly angled.

Mandibular advancement device 100 also includes connecting arm 450 that pivotably and slidably couples upper and lower trays 105, 110 together. As shown, connecting arm 450 is pivotably and slidably held in place by flange 220 of coupling posts 120, 125. Slots 455, 460 of connecting arm 450 enables upper and lower trays 105, 110 to pivot and slide with respect to each other or to plane 410. In some embodiments, the width of slots 455, 460 is wider than the width of flange 220. This allows flange 220 to be inserted through slots 455, 460 when flange 220 and slots are parallel to each other. When flange 220 and slots 455, 460 are not parallel to each other, which is the case when MA device 100 is in the patient's mouth, connecting arm 450 is held in place by flange 220 since it is angled at approximately 107.5° degrees with respect to plane 410. To remove connecting arm 450 and uncouple upper tray 105 from lower tray 110, connecting arm 450 (and upper tray 105) has to swing back until flange 220 is parallel with slot 455, 460 (see FIG. 5).

Figure 5:
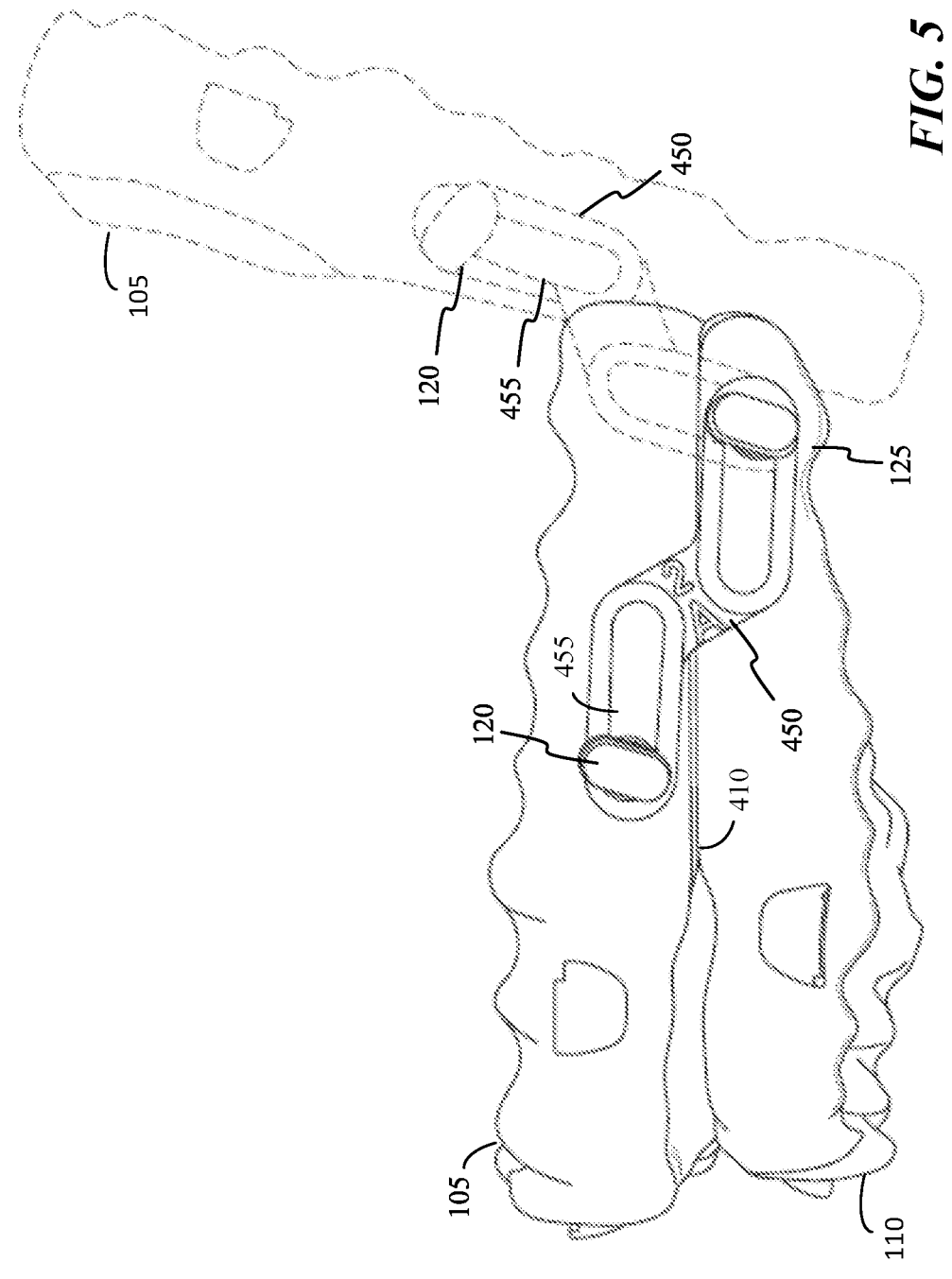
FIG. 5 is a side view of a mandibular advancement device shown in both a closed and opened position in accordance with some embodiments of the present disclosure.

FIG. 5 is a side view of MA device 100 in a closed and opened positions in accordance with some embodiments of the present disclosure. In a closed position, connecting arm 450 is held securely in place by flanges 220 of coupling posts 120, 125. To uncouple the upper and lower trays 105, 110 from each other, upper tray 105 would have to swing back (open) by greater than 45° degrees, which is larger than physically possible if MA device 100 remains in the patient's mouth. In the embodiment shown, flanges 220 are approximately at 50-165 degrees with respect to plane 410. For example, flange 220 can be angled at 107 degrees as shown. In this way, upper and lower trays 105, 110 are securely held in place by connecting arm 450 whenever MA device 100 is in the patient's mouth. This greatly reduces or eliminates the chance of an accidental decoupling of the upper and lower trays 105, 110 during sleep or even when the patient yawns.

Once MA device 100 is removed from the mouth, it can be decoupled by rotating the upper or lower tray 105, 110 until flange 220 of coupling post 120 is parallel with slot 455 or flange 220 of coupling post 125 is parallel with slot 455.

Figure 6:
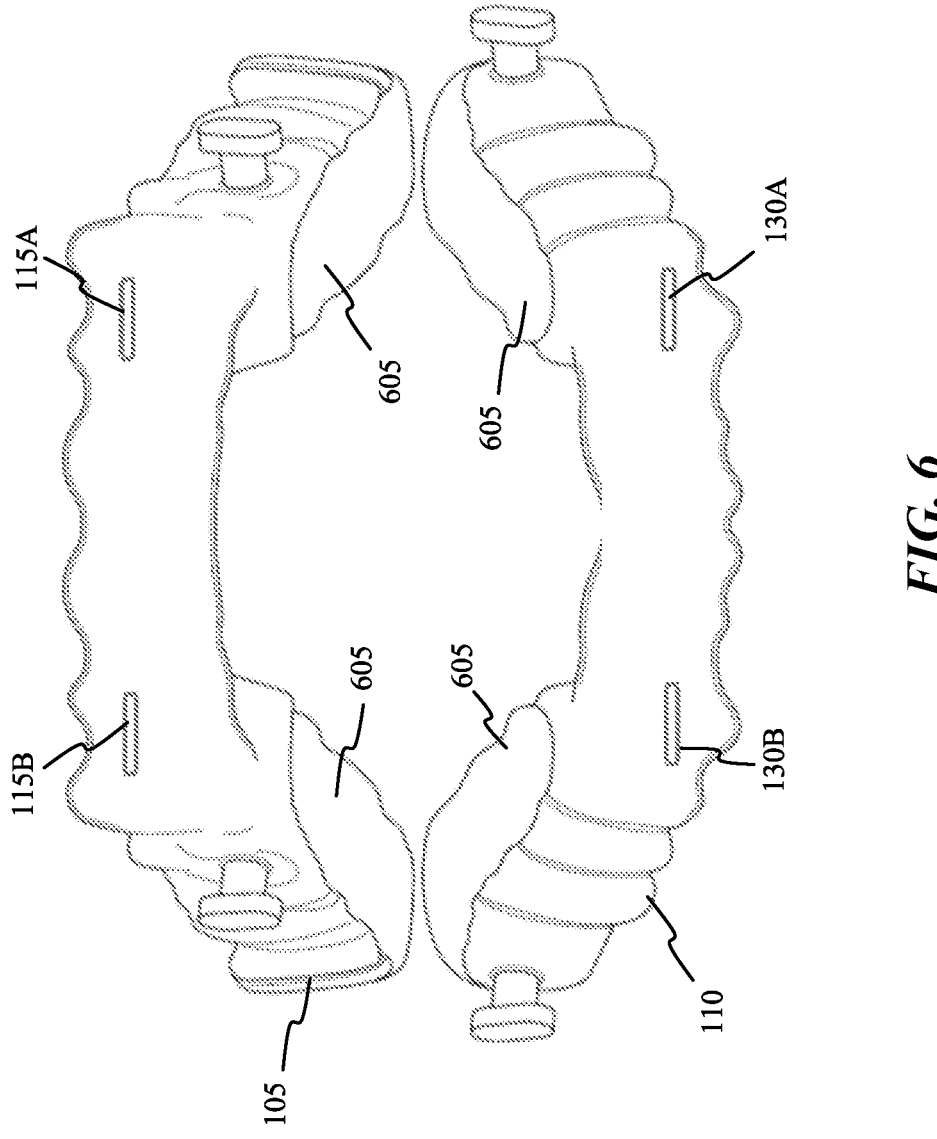
FIG. 6 is a front view of an uncoupled mandibular advancement in accordance with some embodiments of the present disclosure.

FIG. 6 is a front view of upper and lower trays 105, 110 decoupled from each other. Each tray includes a flat surface 605 over the molar and pre-molar areas. The flat surface can also be over the molar area only. Flat surfaces 605 enables upper and lower trays 105, 110 to easily slide over each other when MA device 100 is in a closed position. In this way, the patient's can comfortably moves his/her jaw back and forth even when upper and lower trays 105, 110 are in contact with each other.

Each of the upper and lower trays 105, 110 can be thermal formed, machined or 3D printed as a single piece. Each tray can be thermal formed, machined or 3D printed as a single piece along with flat surface 605 and/or tray-removal features (e.g., 115, 130).

As shown in FIG. 6, tray-removal features 115, 130 can be grooves or channels fabricated into the buccal surface of each tray. The groove can be large enough for the patient's fingernail to catch on and pull off the tray. As previously mentioned, tray-removal features 115, 130 can also be a raised edge or other surface features that can provide some grip.

Figure 7A:
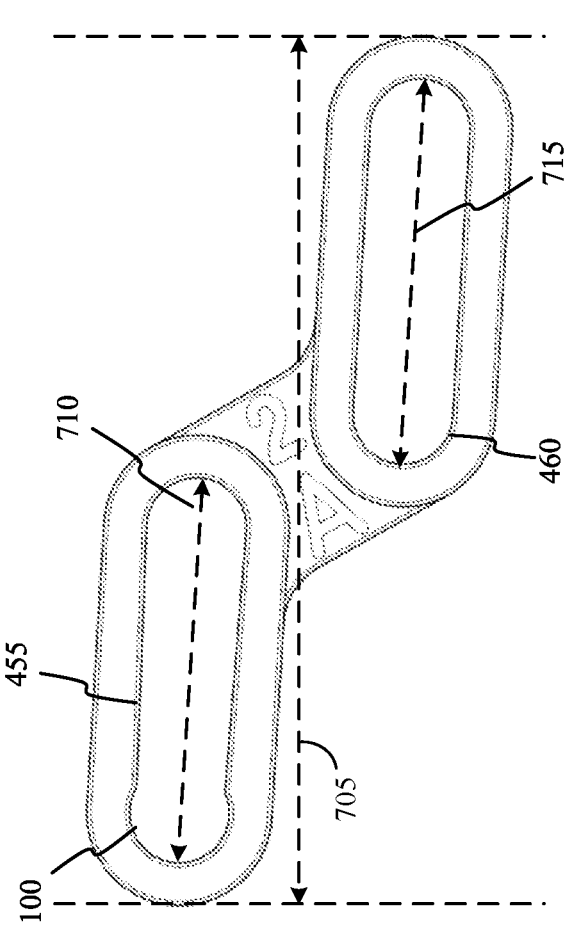
FIG. 7A is a side view of a connecting arm in accordance with some embodiments of the present disclosure.
Figure 7B:
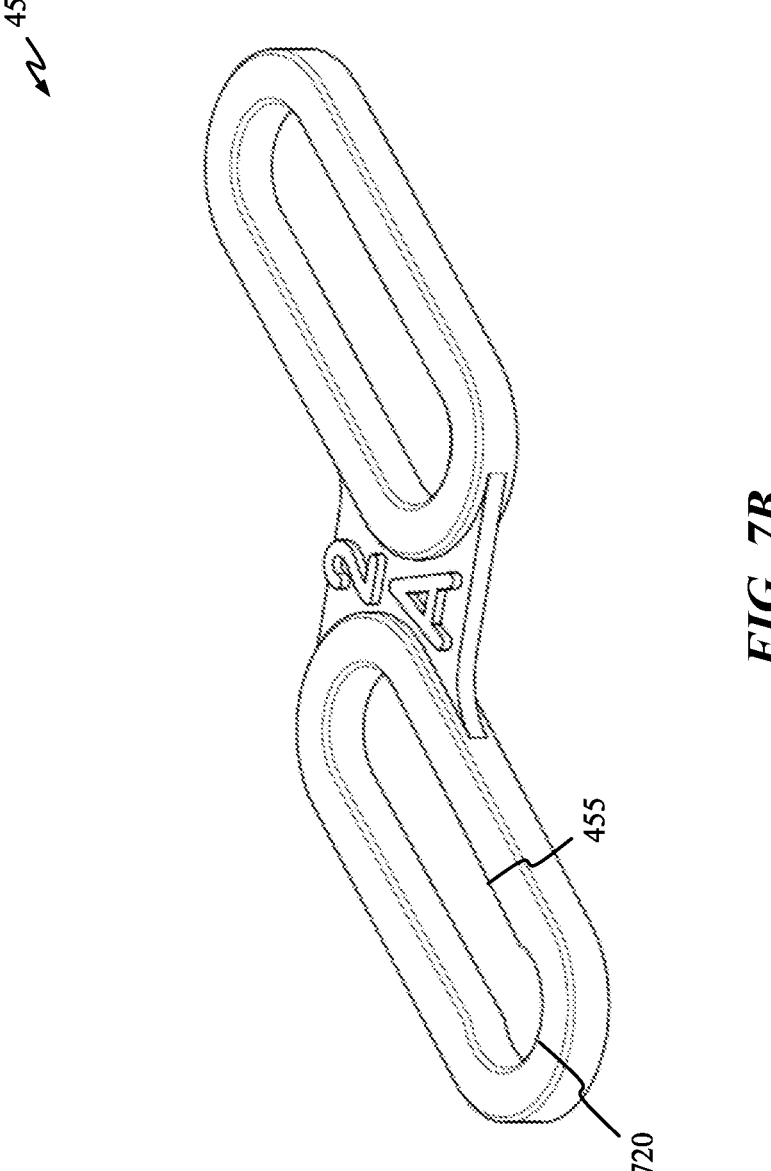
FIG. 7B is a perspective view of the connecting arm in accordance with some embodiments of the present disclosure.

FIG. 7A illustrates connecting arm 450 in accordance with some embodiments of the present invention. FIG. 7B is a perspective view of connecting arm 450 shown in FIG. 7A. Connecting arm 450 includes two parallel slots 455, 460. The width of each slot can be larger than the width of flange 220. The length 710, 715 slots 455, 460 can be the same or they can be different. Connecting arm 450 has an overall length 705, which dictates the amount of movement between upper and lower trays 105, 110. Length 705 of connecting arm 450 also determines the amount of advancement (push forward to the front of the mouth) of lower tray 110 with respect to upper tray 105. In this way, the lower jaw can be advanced by a predetermined amount, which can be adjusted by adjusting length 705. In some embodiments, the total length 705 of connecting arm 450 can be adjustable. For example, the upper portion (where slot 455 resides) and the lower portion of connecting arm can be coupled together by a length-adjustable junction (not shown). In this way, the patient can adjust the amount of forward advancement of the lower jaw as desired. Alternatively, the patient can be provided with a plurality of connecting arms 450 of different lengths.

Connecting arm 450 can have an overall Z-like shape with slots 455, 460 being separate of each other. In some embodiments, slots 455, 460 can be one continuous slot with two parallel portions being connected together by a center portion. The center portion can be angled as shown in FIG. 7A or it can be perpendicular to the two parallel portions.

In some embodiments, one or more slots 455, 460 can include a larger opening at the far end of the slot. For example, slot 455 can have circular opening 720 at the far end, which is away from the center of connecting arm 450. The diameter of circular opening 720 can be larger than the width of slot 455.

Figure 8:
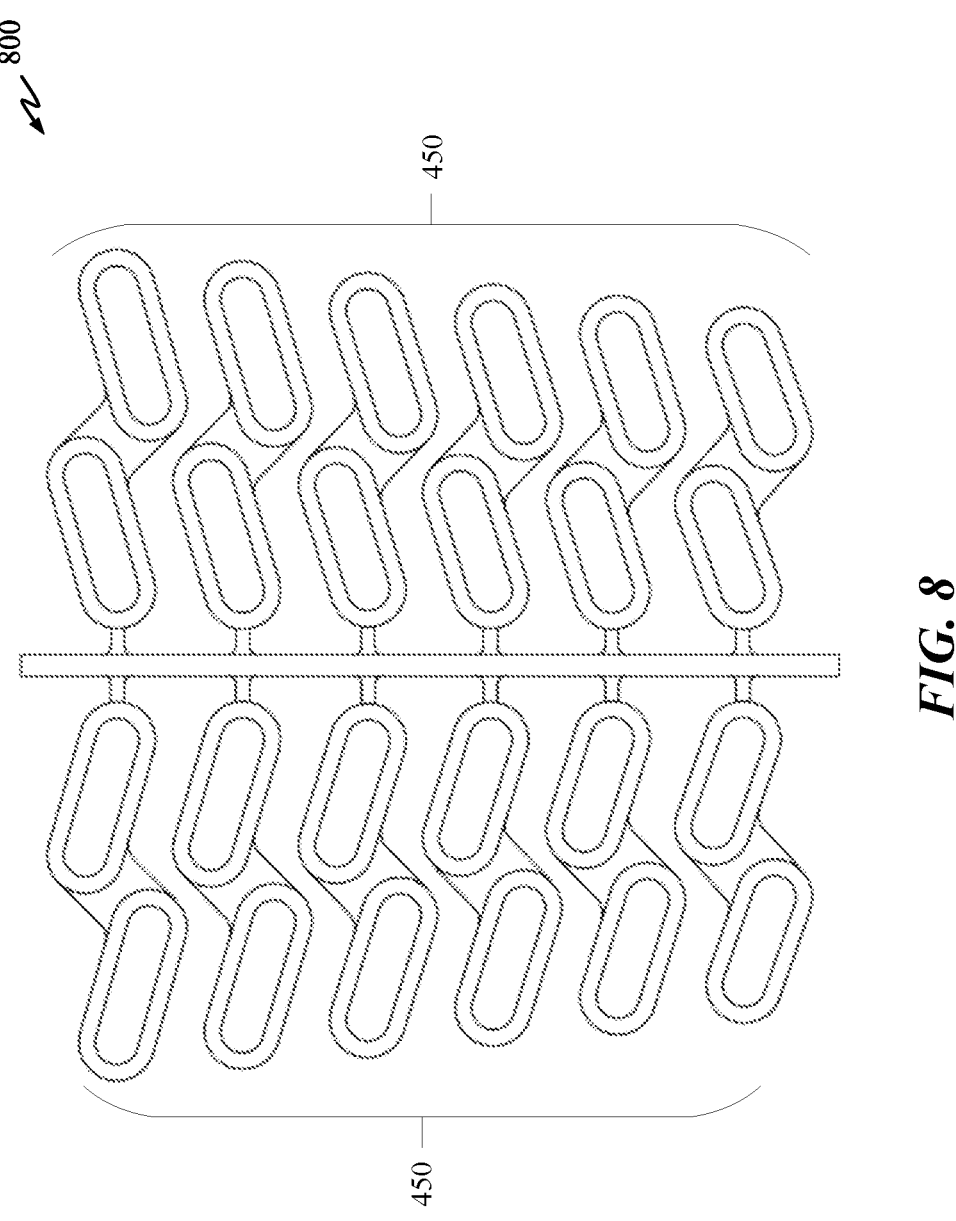
FIG. 8 is a top view of a fabrication arrangement for the connecting arms in accordance with some embodiments of the present disclosure.

FIG. 8 illustrates a fabrication arrangement 800 in which a plurality of connecting arms 450 can be manufactured. Connecting arms 450 can be injection molded. Some of the connecting arms 450 can have different lengths to allow medical or dental practitioner to design different treatment options.

One or more of the components, steps, features, and/or functions illustrated in the figures may be rearranged and/or combined into a single component, block, feature or function or embodied in several components, steps, or functions. Additional elements, components, steps, and/or functions may also be added without departing from the disclosure. The apparatus, devices, and/or components illustrated in the Figures may be configured to perform one or more of the methods, features, or steps described in the Figures. The algorithms described herein may also be efficiently implemented in software and/or embedded in hardware.

Reference in the specification to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment.

Some portions of the following detailed description are presented in terms of algorithms and symbolic representations of operations on data bits within a computer memory. These algorithmic descriptions and representations are the methods used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared or otherwise manipulated. It has proven convenient at times, principally for reasons of common usage, to refer to these signals as bits, values, elements, symbols, characters, terms, numbers or the like.

It should be borne in mind, however, that all of these and similar terms are to be associated with the appropriate physical quantities and are merely convenient labels applied to these quantities. Unless specifically stated otherwise as apparent from the following disclosure, it is appreciated that throughout the disclosure terms such as "processing," "computing," "calculating," "determining," "displaying" or the like, refer to the action and processes of a computer system, or similar electronic computing device, that manipulates and transforms data represented as physical (electronic) quantities within the computer system's registers and memories into other data similarly represented as physical quantities within the computer system's memories or registers or other such information storage, transmission or display.

The figures and the following description describe certain embodiments by way of illustration only. One skilled in the art will readily recognize from the following description that alternative embodiments of the structures and methods illustrated herein may be employed without departing from the principles described herein. Reference will now be made in detail to several embodiments, examples of which are illustrated in the accompanying figures. It is noted that wherever practicable similar or like reference numbers may be used in the figures to indicate similar or like functionality.

The foregoing description of the embodiments of the present invention has been presented for the purposes of illustration and description. It is not intended to be exhaustive or to limit the present invention to the precise form disclosed. Many modifications and variations are possible in light of the above teaching. It is intended that the scope of the present invention be limited not by this detailed description, but rather by the claims of this application. As will be understood by those familiar with the art, the present invention may be embodied in other specific forms without departing from the spirit or essential characteristics thereof. Likewise, the particular naming and division of the modules, routines, features, attributes, methodologies and other aspects are not mandatory or significant, and the mechanisms that implement the present invention or its features may have different names, divisions and/or formats.

Additionally, the present invention is in no way limited to implementation in any specific programming language, or for any specific operating system or environment. Accordingly, the disclosure of the present invention is intended to be illustrative, but not limiting, of the scope of the present invention, which is set forth in the following claims.

The invention claimed is:

1. A dental appliance for snore reduction, the dental appliance comprising:

an upper tray configured to engage a plurality of maxillary teeth, the upper tray comprises a first coupling post located on a buccal surface of the upper tray;

a lower tray configured to engage a plurality of mandibular teeth, the lower tray comprises a second coupling post located on a buccal surface of the lower tray, wherein the first coupling post is closer to a midline of the upper tray than the second coupling post;

one or more tray-removal features disposed on a buccal or lingual surface of each of the upper and lower trays, each of said one or more tray-removal features comprising a raised ridge having a top portion extending outward in a buccal direction from the buccal surface or a lingual direction from the lingual surface of the upper or lower tray, thereby defining an edge to be grasped by the patient; and a connecting arm configured to couple the upper and lower trays, the connecting arm comprises a first slot and a second slot, wherein one or more of the first and second coupling posts comprise a flange configured to pivotably and slidably secure the connecting arm and to release the connecting arm when it is rotated to a predetermined angle with respect to a closed position of the upper and lower trays, wherein the predetermined angle is larger than 45 degrees.

2. The dental appliance of claim 1, wherein the first and second slots are parallel to each other.

3. The dental appliance of claim 1, wherein both of the first and second coupling posts comprise a flange.

4. The dental appliance of claim 1, wherein the flange comprises a width smaller than a width of each of the first and second slots and a length longer than the width of each of the first and second slots.

5. The dental appliance of claim 4, wherein each of the first and second coupling posts comprises a T-shape post.

6. The dental appliance of claim 1, wherein the one or more tray-removal features are disposed on the buccal surface of each of the upper and lower trays.

7. The dental appliance of claim 1, wherein the one or more tray-removal features are disposed on a lingual surface of each of the upper and lower trays.

8. The dental appliance of claim 1, wherein the upper tray comprises a flat-bottom surface, and wherein the lower tray comprises a flat-upper surface, wherein the flat-bottom and flat-upper surfaces are parallel to each other when the upper and lower trays are in the closed position.

9. The dental appliance of claim 1, wherein the predetermined angle is larger than 90 degrees.

10. A dental appliance for adjusting a position of a lower jaw, the dental appliance comprising:

an upper tray configured to engage a plurality of maxillary teeth, the upper tray comprises a first coupling post located on a buccal surface of the upper tray and a flat-bottom surface;

a lower tray configured to engage a plurality of mandibular teeth, the lower tray comprises a second coupling post located on a buccal surface of the lower tray and a flat-upper surface, wherein the first coupling post is closer to a midline of the upper tray than the second coupling post, and wherein the flat-upper and flat-bottom surfaces are parallel to each other when the upper and lower tray are in a closed position;

a one or more tray-removal features disposed on a buccal or lingual surface of each of the upper and lower trays, each of said one or more tray-removal features comprising a raised ridge having a top portion extending outward in a buccal direction from the buccal surface or a lingual direction from the lingual surface of the upper or lower tray, thereby defining an edge to be grasped by the patient; and a connecting arm configured to couple the upper and lower trays, the connecting arm comprises a first slot and a second slot parallel to each other.

11. The dental appliance of claim 10, wherein one or more of the first and second coupling posts comprise a flange configured to pivotably and slidably secure the connecting arm and to release the connecting arm when it is rotated to a predetermined degree with respect to a closed position of the upper and lower trays, wherein the predetermined degree is larger than 45 degrees.

12. The dental appliance of claim 10, wherein each of the first and second coupling posts comprises a T-shape post.

13. The dental appliance of claim 12, wherein the T-shape post comprises a flange having a width smaller than a width of each of the first and second slots and a length longer than the width of each of the first and second slots.

14. A dental appliance for adjusting a position of a lower jaw of a patient, the dental appliance comprising:

an upper tray configured to engage a plurality of maxillary teeth, the upper tray comprises a first coupling post located on a buccal surface of the upper tray;

a lower tray configured to engage a plurality of mandibular teeth, the lower tray comprises a second coupling post located on a buccal surface of the lower tray, wherein each of the first and second coupling posts comprises a flange configured to pivotably and slidably secure a connecting arm and to release the connecting arm when the upper tray is rotated to a predetermined angle with respect to a closed position of the upper and lower trays;

one or more tray-removal features disposed on a buccal or lingual surface of each of the upper and lower trays, each of said one or more tray-removal features comprising a raised ridge having a top portion extending outward in a buccal direction from the buccal surface or a lingual direction from the lingual surface of the upper or lower tray, thereby defining an edge to be grasped by the patient; and wherein the connecting arm is configured to couple the upper and lower trays, the connecting arm comprises a first slot and a second slot parallel to each other.

\* \* \* \* \*